(12) United States Patent
Williams

(10) Patent No.: US 8,575,155 B2
(45) Date of Patent: Nov. 5, 2013

(54) COMPOSITION AND METHOD TO MODIFY SPERM FUNCTION AND INCREASE MALE GENDER RATIO IN MAMMALS

(76) Inventor: Timothy James Williams, Arcola, IL (US)

( * ) Notice: Subject to any disclaimer, the term of this patent is extended or adjusted under 35 U.S.C. 154(b) by 50 days.

(21) Appl. No.: 12/733,928

(22) PCT Filed: Nov. 26, 2008

(86) PCT No.: PCT/IB2008/003920
§ 371 (c)(1),
(2), (4) Date: Mar. 25, 2010

(87) PCT Pub. No.: WO2009/104053
PCT Pub. Date: Aug. 27, 2009

(65) Prior Publication Data
US 2010/0234676 A1     Sep. 16, 2010

(51) Int. Cl.
*A61K 31/54* (2006.01)
(52) U.S. Cl.
USPC .................................. 514/224.8; 514/227.5

(58) Field of Classification Search
USPC ........................................ 514/224.8, 227.5
See application file for complete search history.

(56) References Cited

U.S. PATENT DOCUMENTS

| | | | |
|---|---|---|---|
| 2002/0090628 A1* | 7/2002 | Gray et al. | 435/6 |
| 2005/0112541 A1* | 5/2005 | Durack et al. | 435/2 |
| 2007/0166694 A1* | 7/2007 | McCauley et al. | 435/2 |

* cited by examiner

*Primary Examiner* — Raymond Henley, III

(57) ABSTRACT

A composition and method is provided for modifying sperm fertility in mammals for the purpose of biasing the gender in favor of male offspring. The composition includes an amount of a class of compounds of phenoxazine or phenothiazine, having the structure (FIG. 1) and ionic derivatives thereof, wherein R1 is H, a lower alkyl group or N(R3)2, R2 is N, S, O, and R3 is H or a lower alkyl group. A second component of the composition is an amount of a hexose sugar or the phosphorylated hexose esters of such. When mixed with living sperm prior to or at the time of insemination, the composition results in modified rates of conception and an alteration of the birth sex ratio.

12 Claims, 3 Drawing Sheets

COMPOSITION AND METHOD TO MODIFY SPERM FUNCTION AND INCREASE MALE GENDER RATIO IN MAMMALS

CROSS-REFERENCE TO RELATED APPLICATIONS

Priority is hereby claimed to, and this application is a national stage entry of PCT/IB08/03920, International filing date Nov. 26, 2008, which entry claims priority to U.S. patent application Ser. No. 12/286,521, filed Oct. 1, 2008, which is incorporated herein.

STATEMENT REGARDING FEDERALLY SPONSORED RESEARCH OR DEVELOPMENT

"Not Applicable"

REFERENCE TO SEQUENCE LISTING, A TABLE, OR A COMPUTER PROGRAM LISTING COMPACT DISC APPENTIX

"Not Applicable".

BACKGROUND OF THE INVENTION

The present invention relates to compositions and methods for treating sperm for the purpose of modifying sperm function and the gender ratio in offspring of mammalian species. The invention is further directed to a method of using the composition to modify the functionality of mammalian sperm in general and more specifically, to increase sperm fertility for the purpose of enhancing conception. In addition, the invention can be used to modify the fertility of X-chromosome and Y-chromosome bearing sperm and using said sperm in the reproduction processes of artificial insemination (AI), in vitro fertilization (IVF), and embryo transfer (ET) for the purpose of modifying gender in mammals.

It is well documented in mammalian species that the X-chromosome contains a unique set of genes which are highly conserved across mammals as well as other vertebrates. One of the X-linked genes codes for the ubiquitous enzyme, glucose-6-phosphate dehydrogenase (G6PDH). G6PDH is a pivotal enzyme in glucose metabolism and is the primary regulator of the hexose-mono phosphate shunt (HMS), also known as the pentose phosphate shunt (PPP). The main function of the HMS is to produce NADPH, which is necessary for reduction-oxidation reactions and to form ribose-5-phosphate for nucleic acid synthesis.

G6PDH also play an important role in glucose oxidation via glycolysis, a primary source of cellular energy. Glucose metabolism is implicated in the fertilization process in many species (mouse, Hoppe, 1976; rat, Niwa and Iritani, 1978; human, Mahadevan et al., 1997, incorporated herein by reference). It is well accepted that glucose metabolism through glycolysis provides energy to sperm. However, the role of glucose metabolism through the hexose-monophosphate shunt (HMS) in spermatozoa is not understood. The existence of an HMS pathway in mouse (Setchell et al, 1969, incorporated herein by reference) and human sperm (Aitken et al, 1997 incorporated herein by reference) has been documented, but not in other species including ram or bull sperm. The techniques used for these early studies have come into question and the evidence does not prove or disprove the existence of the HMS in sheep or cattle sperm.

The implications of a functioning HMS in sperm, as found in human and mouse sperm, however does suggests that it is implicated in sperm function. Since NADPH metabolism has been implicated in sperm motility and fertilization, it has been suggested that the HMS is a key metabolic pathway in sperm capacitation, the acrosome reaction, and oocyte fusion (Urner, F. and Sakkas, D., 1999, incorporated herein by reference).

While investigating the role of the X-linked enzyme, G6PDH, and the HMS as a method to sex mouse embryos, I first used the phenoxazine compound, brilliant cresol blue (BCB) in living embryos to detect and semi-quantify G6PDH activity (Williams, 1986, incorporated herein by reference) and successfully transplant these embryo to produce normal living offspring. This study demonstrated that BCB and its metabolites were relatively non-toxic in the early-staged mouse embryos. My studies with bovine embryos revealed similar results. While investigating the HMS in bovine oocytes, Tiffen et al., 1991, (incorporated herein by reference) demonstrated that the phenoxazine/phenothiazine class of compounds could be used to increase glucose oxidation specifically through the Hexose Monophosphate Shunt (HMS). They also saw an increased level of glucose metabolism through glycolysis. These authors documented that BCB causes a 15-fold increase in oxidation of glucose through the HMS and a somewhat less increase through glycolysis.

It is well documented that early staged female embryos exhibit preferential metabolism of glucose via the HMS and that male embryos preferential use glycolysis (Tiffin et al., 1991, Kimura et al, 2005, incorporated herein by reference). This is due to the presence of two X-chromosomes and elevated levels of G6PDH in the female. Male embryos have a single X-chromosome and low levels of G6PDH.

My postulate is that the sexual dimorphism in glucose metabolism extends to the sperm and spermatocytes. This would mean that levels of the X-linked enzyme, G6PDH, are very low in the Y-chromosome bearing sperm due to the absence of the X-chromosome. Given this assumption, the Y-chromosome bearing sperm (similar to male embryo) cannot oxidize glucose or G-6-P through the HMS, but oxidizes large amounts of G-6-P through glycolysis. Since phenoxazine catalyzes glycolysis it is hypothesized that the addition of G-6-P and phenoxazine further amplifies glycolysis and leads to increased ATP production, capacitation, motility, and the observed increase in fertility of the Y-chromosome bearing sperm.

In the X-chromosome bearing sperm, assumed to have high levels of G6PDH due to the presence of the X-chromosome, G-6-P would be metabolized through the HMS. However, when exposed to the composition of this invention, the oxidation of G-6-P appears inhibited and results in reduced fertility levels and fewer female offspring. This inhibition through the HMS is likely due to a modified redox potential caused by the oxidant chromo-phenoxazine and the absence of an electron transfer agent such as NADPH oxioreductase resulting in a rate limiting turnover (oxidation) of endogenous NADPH. Without the reductive power of NADPH, the chromo-phenoxazine remains in the oxidative state and quenches the HMS. In the presence of phenoxazine (without a NADPH oxioreductase or a similar electron transfer agent), oxidation of G-6-P is shutdown resulting in an inhibition of ATP production and a loss of sperm motility and sperm function specific to the X-chromosome bearing (female) sperm.

Another factor influencing the X-chromosome bearing (female) sperms preferential oxidization of G-6-P through the HMS pathway is the major cofactor NADP+ which also regulates the pathway. This cofactor is needed in the first and third steps of the HMS pathway. Without the replenishment of NADP+ by the recycling of NADPH (due the oxidative state of the cell) the pathway would quickly become inhibited and eventually quench resulting in a loss in needed energy precursors. This could contribute to the X-chromosome bearing (female) sperm losing function, motility, and fertilization capacity.

Another observation I have made is that sperm exposed to phenoxazine compounds without added substrates quickly lose sperm motility and subsequent fertility. This loss of motility is likely due to a quenching of energy metabolism of the cell including glycolysis and the HMS, but more importantly the loss of ATP production via quenching of oxidative phosphorylation and respiratory potential. The result is little or no motility and a potential loss of fertilization capacity regardless of sperm gender. This observation points to the role of chromo-phenoxazine in quenching or slowing the respiratory cycle which is dependent upon large amounts of reducing power in the form NADH.

Patent documents of interest concerning methods to preferentially modify sperm function include: U.S. Pat. Nos. 4,191,749, 4,191,749, 4,999,283, 4,788,984, 6,627,655, and 20070166694

Patent documents of interest concerning the use of phenoxazine BCB in living tissue are limited to in vitro assays, dye indicators, and staining methodology. These include: U.S. Pat. Nos. 6,790,411, 6,867,015, 6,967,015, 6,420,128, and 4,622,395.

Patent documents of interest related to methods of modifying sex ratio in mammals by cell sorting technology include: U.S. Pat. Nos. 6,524,860, 6,372,422, 6,149,867, 6,071,689, and 5,135,759.

Patent documents of interest related to modifying sex ratio in mammals by antigen or antibody sorting include: U.S. Pat. Nos. 6,489,092, 6,153,373, 5,660,997, and 5,439,362.

TERMINOLOGY

G6PDH: glucose-6-phosphate dehydrogenase
NADP+: tri-phospbopyridine nucleotide
NADPH: beta-nicotinamide adenine dinucleotide phosphate or tri-phosphopyridine nucleotide
NADH: beta-nicotinamide adenine dinucleotide
G-6-P: D-glucose-6-phosphate
6-PG: 6-phosphoglutamate
chromo-Phenoxazine: Phenoxazine (oxidized form)
leuco-Phenoxazine: Phenoxazine (reduced form)
RMS: Hexose monophosphate shunt

BRIEF SUMMARY OF THE INVENTION

In summary, the present invention comprises a composition and method for modifying sperm function, more specifically for modifying the sperm motility, capacitation, and/or fertility of both the X-chromosome bearing sperm (female) and the Y-chromosome bearing sperm (male), and providing a method for modifying sex ratio in mammals by exposing living mammalian sperm prior to artificial insemination to the composition. This composition consists of a chromo-phenoxazine compound wherein said compound is Brilliant Cresyl Blue, i.e., 2-methyl-3-diethylamino-7-amino phenoxazine, and a hexose ester or phosphorylated hexose ester compound wherein said compound is D-glucose-6-phosphate. Cattle, horse, pig, buffalo, alpacas, llamas, dog, cats, goats, and sheep semen are primary examples of such mammalian sperm.

The method comprises a first step of placing a sample of semen, either fresh or frozen, into a vial, ampoule, or tube, or the like together with the composition of matter. The sperm and said composition are mixed and incubated at the appropriate temperature to maintain sperm viability and for a selected time. The temperature is generally at or near body temperature, e.g. 35-39° C. for cattle, and the time is generally less than 60 minutes but is experimentally determined, and varies with the species, sperm concentration, volume of the sperm sample, and with other factors such as type of diluent, and whether the sperm have been frozen, chilled, or freshly collected. Successful treatment of the sperm sample is determined by experimental observation. The treated sperm are inseminated by standard artificial methods usually consisting of introducing the sperm sample into the reproductive tract of a receptive female. A second possibility is to introduce the treated sperm into an in vitro fertilization system for the purpose of producing embryos for subsequent transfer to a receptive female. A third embodiment is to treat the sperm prior to cryopreservation. Further, a kit embodiment of the composition of matter and method of application is described.

DETAILED DESCRIPTION OF THE INVENTION

The details of the subject composition, the preparation of composition, and the method of use of the composition are described herein. The subject invention is also described as a kit embodiment and includes the method of use of this embodiment. Before the subject invention is described, it is best understood that the invention is not limited to particular the embodiments described below. Variations of the particular embodiments maybe made and still fall within the scope of the appended claims. It is also to be understood that the terminology employed is for the purpose of describing particular embodiments, and is not intended to be limiting. Instead, the scope of the present invention is established by the appended claims.

Compositions

Figure 1:
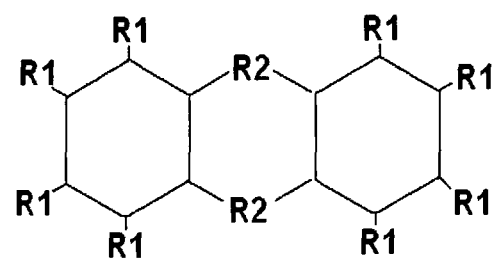
FIG. 1 is a schematic formula of the chromo-phenoxazine and phenothiazine class of compounds, the embodiment having been selected from this class of compounds and having the structure indicated and ionic derivatives thereof, wherein R1 is H, a lower alkyl group or N (R3)2, R2 is N, S, O, and R3 is H or a lower alkyl group.
Figure 2:
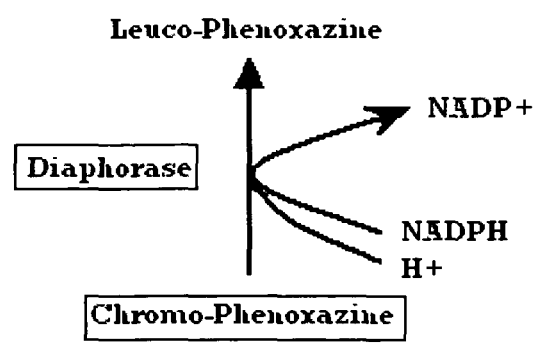
FIG. 2 is diagram of the chemical reduction of chromo-phenoxazine to leuco-phenoxazine in the presence of the NADH.

The present invention includes within the material components a composition for use with living cells or sperm of mammals. Included within the composition of said embodiment is a phenoxazine or phenothiazine compound having the structure found in FIG. 1 and ionic derivatives thereof, wherein R1 is H, a lower alkyl group or N(R1)2; R2 is N, S, or O; and R3 is H or a lower alkyl group. The primary use of this embodiment within the invention is as an electron accepting agent within living mammalian sperm for the purpose of catalyzing the glycolysis pathway. The electron transfer agent is a compound or molecule that transfers an electron, such as the hydride ion, from a reduced enzyme cofactor, beta-nicotinamide adenine dinucleotide phosphate (NADPH) or beta-nicotinamide adenine dinucleotide (NADH) to an oxidant compound such as a chromo-phenoxazine compound. FIG. 2 is a diagram of the reduction of chromo-phenoxazine to leuco-phenoxazine. This process acts as a catalyst for amplification of metabolic processes that rely on the reducing power of NAD(P)H to NAD(P+).

The phenoxazine or phenothiazine compounds must be provided in a composition and concentration such that they are non-toxic to living sperm and in the initial composition and the metabolic derivatives such that they exert the required physiological effect. Variants of this use aspect of the invention could be selected from these groups but are not limited to these embodiments; phenoxazine components such as Brilliant Cresyl Blue, i.e., 2-methyl-3 diethylamino-7-amino phenoxazine and related embodiments, e.g., 7-(Diethyl amino)-3-amino-8-methyl-3H-phenoxazine hydrochloride, and 7-Amino-3-(diethyl amino)-2-methylphenoxazine-5-ium chloride, phenoxazine, Capri Blue (C.I. 51000), benzo-a-phenozoxanium (Meldora(medola) Blue), Nile Blue (C.I. 51180), Acid Blue 90, Brilliant Blue G, Brilliant Blue C, Basic Blue 3, and Coomassie Brilliant Blue C-250. Phenothiazine embodiments are Methylene Blue (C.I. 52015), Methylene Green, Azure A, Azure B (C. I. 52010), Azure C, Lauth's Violet (C. I. 52000), Thiocarmine R (C.I. 52035), and Toluidine Blue O.

The second component of the composition is a hexose sugar or the phosphorylated hexose esters of such which act as an energy source for glycolysis and the HMS pathways. Included reagents are glucose, mannose, fructose, and galactose, and their phosphorylated esters, D-glucose-6-phosphate, fructose-6-phosphate, mannose-6-phosphate, and galactose-6-phosphate. Of primary utility in this invention is D-glucose-6-phosphate (G-6-P). D-glucose-6-phosphate has a triple role in this invention acting as (a) the oxidative substrate for the Hexose monophosphate shunt (HMS); (b) as the inducer of the hexose monophosphate transport system and (c) as the phosphorylated glucose precursor in glycolysis. As the primary oxidative substrate of the hexose monophosphate shunt (HMS), G-6-P becomes the primary hydrogen donor for the production of beta-nicotinamide adenine dinucleotide phosphate (NADPH) in the HMS pathway. This pathway is particularly relevant to glucose metabolism in the X-chromosome bearing (female) sperm.

Another function of D-glucose-6-phosphate in this invention is induction of the hexose monophosphate transport system and cellular uptake of D-glucose-6-phosphate. Incubation of cells in a hexose-6-phosphate compound at the appropriate media concentrations can causes induction of the hexose monophosphate transport system and direct cellular uptake of D-glucose-6-phosphate. This uptake is independent of the glucose transport system requiring phosphorylation of glucose. While the mechanism of the transport is unknown, there are other known examples of hexose monophosphate transport inducers. These include, but are not limited to, mannose-6-phosphate and fructose-6-phosphate and D-glucose-6-phosphate.

A third function of D-glucose-6-phosphate is to act as the initial energy substrate for energy production in the form of ATP and NADH production through direct oxidation via the glycolysis pathway and subsequent respiratory metabolism.

Figure 3:
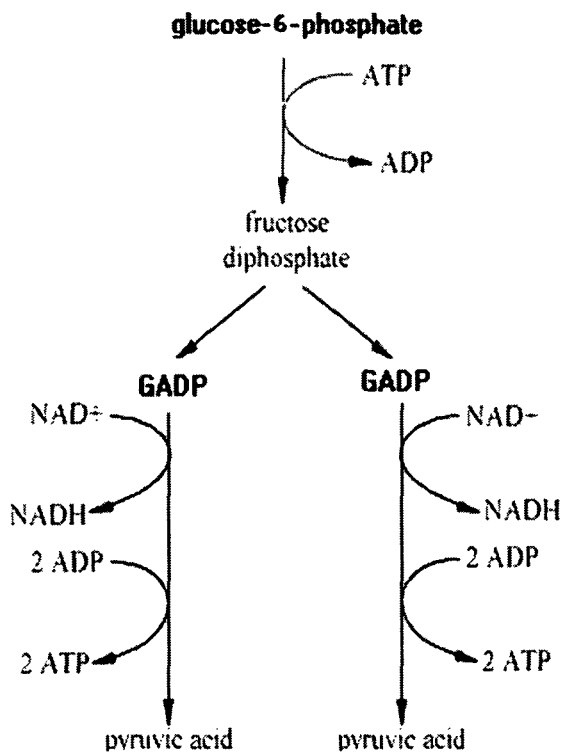
FIG. 3 is a diagram of the glycolysis pathway through which D-glucose-6-phosphate is oxidized showing the oxidation of NAD+ and two possible points of amplification by the said composition resulting in the reduction of chromo-phenoxazine.

FIG. 3 illustrates in summary the glycolytic pathway and the oxidation of G-6-P to pyruvate in which 2 moles of NAD+ are reduced provide regeneration of reducing equivalents in the form of NADH. It is at this point that chromo-phenoxazine acts as an electron accepting agent and catalyzes the oxidation of G-6-P during glycolysis. Through glycolysis, each mole of G-6-P is oxidized to two moles of pyruvate which are subsequently metabolized in the TCA cycle to produce more NADH equivalents which provide the reduction potential for oxidative phosphorylation and ATP production within the mitochondria. The NADH equivalents stimulate sperm function, motility and increased ATP production provides the energy for increasing sperm metabolism and motility.

As stated above, this component should be provided in purity and concentration such that it is non-toxic to living mammalian cells and sperm, but yet has the needed physiological consequence.

Figure 4:
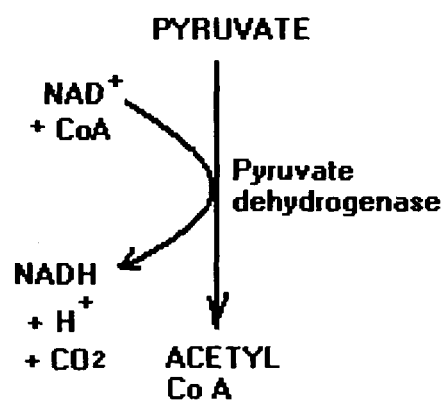
FIG. 4 is a diagram of the oxidative decarboxylation of pyruvate to acetyl CoA which links glycolysis to the citric acid cycle as another example of amplification by said composition.

FIG. 4 is a diagram of the oxidative decarboxylation of pyruvate to acetyl CoA which links glycolysis to the citric acid cycle. This is another example of an important point of metabolic amplification by said composition through the reduction of NAD+ to NADH. The metabolic reaction is mediated by pyruvate dehydrogenase. This enzyme would be of equal titer in male and female spermatozoa and would not in itself be a point of differential metabolism. However, the excess production of pyruvate by preferential glycolysis in the Y-chromosome bearing (male) sperm along with an excess of NAD+ (due to the quenching effect of the reduction of phenoxazine) would stimulate the increased metabolism of pyruvate into the citric acid cycle in Y-chromosome bearing (male) sperm.

Figure 5:
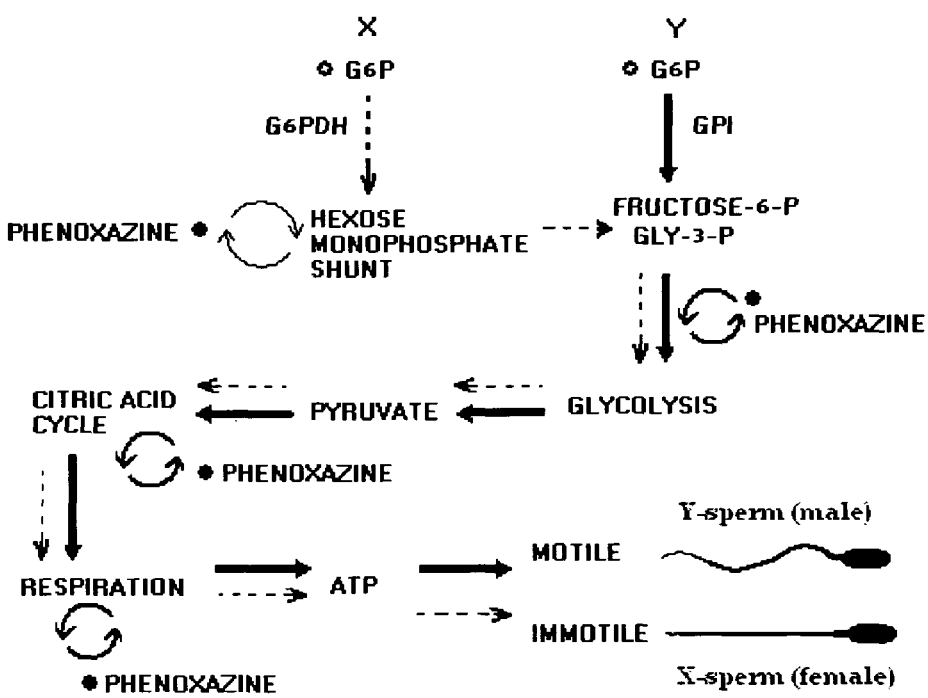
FIG. 5 is a schematic diagram of the metabolic pathways that are modified by the composition of matter embodied within this invention resulting in increased sperm function of the Y-chromosome bearing (male) sperm.

FIG. 5 is a schematic diagram of how the components of the invention initiate the biological response in the X and Y-chromosome bearing sperm. The transfers of electrons through the metabolic pathways of the X-chromosome bearing (female) sperm are represented by the light dotted arrows. When the semen mixture, containing relatively equivalent amounts of X and Y-bearing sperm, is exposed the substrate, G-6-P, both the X and Y-chromosome bearing sperm (represented by the X and Y, respectively) are stimulated by the uptake of G-6-P. Because the X-chromosome bearing (female) sperm retains a high titer of the potent X-linked enzyme, G6PDH, it will shunt the G-6-P into the HMS pathway. However, without the presence of an electron transfer agent such as NADH oxidoreductase enzyme or a similar transfer agent, the HMS would utilize the G-6-P without recycling of NADP+. (The low level of phenoxazine reduction is indicated by the light circular arrows.) The result is a loss of fertility and motility of the female sperm due the quenching action of the still oxidized chromo-phenoxazine compound on respiration, the production of ATP, and subsequent sperm function.

The transfers of electrons through the metabolic pathways of the Y-chromosome bearing (male) sperm are represented by the solid-line arrows in FIG. 5. The Y-chromosome sperm (represented by the Y) does not have the X-linked enzyme, G6PDH. With little or no intercellular levels of the enzyme, the male sperm are unable to initiate metabolism of the G-6-P through the HMS pathway. The G-6-P is shunted directly into the glycolytic pathway. As glycolysis proceeds, it is stimulated (FIG. 3), here represented by dark circular arrows, as result of the direct reduction of chromo-phenoxazine (FIG. 2) and the production of reducing equivalents in the form of NADH. The metabolic stimulation of the Y-chromosome bearing (male) sperm would continue at the point of oxidative decarboxylation of pyruvate, and continue into respiration. The metabolic results would be an increase in reductive potential of the cell, a stimulation of respiration by the reduction of the chromo-phenoxazine component, i.e., removing the quenching effects of phenoxazine, and increased sperm function, motility, and fertilization capacity of the Y-chromosome bearing (male) sperm.

Upon insemination of the sperm treated with the composition of this invention, the Y-chromosome bearing (male) sperm would have increased metabolic capacity relative the X-chromosome bearing (female) sperm. The sperm will competitively sort themselves in the reproductive tract of the female with the Y-chromosome bearing (male) sperm having a higher probability of fertilization. The result is a shifting of the sex ratio in favor of male offspring.

Preparation of the Composition

The composition described above is fabricated employing numerous protocols. The biologically active nature of the components requires stabilization for maintenance of bioactivity. The composition of matter can be stabilized by lyophilization (drying), sulfate inhibition, or by freezing of a composition mixture. In one form, each compound of the composition is prepared and stored in separate instruments. Prior to use, each compound is mixed with a buffered solution in the appropriate concentrations to produce a reagent mixture. In another form of embodiment, the subject composition could be maintained in the liquid state and stabilized at temperatures at or below 0° C., usually below −15° C. or lower. In another embodiment, the individual aliquots of said composition could be mixed with the cell or sperm sample prior to freezing of the sperm sample. In other embodiments, the individual compounds of the composition are stabilized by lyophilization (freeze-drying) and packaged either in multiple, bulk or individual quantities of required aliquots. Prior to use, each compound is mixed in the appropriate concentrations to produce the composition. In other embodiments, the individual compounds of the composition are mixed to form a single composition prior to storage; stabilization is done by freezing as described in the above embodiment. Alternatively, the single composition could be stabilized by lyophilization (freeze-drying) in multiple, bulk, or individual quantities of required aliquots.

Composition in Kit Form

The invention includes a method of use of this invention in kit form. This embodiment requires the composition be prepared in unit dosage forms. For example, the composition is provided in concentrated form, either in solution or dried (lyophilized), packaged such that when a sperm sample is added to the composition container, and the resulting composition solution is of the appropriate physiological concentration. The mixture of sperm and composition are then incubated within the composition container (e.g., a 0.5 mL sample vial). Alternatively, the mixture can be returned to the semen container (e.g., a 0.5 mL semen straw) and incubated within the semen straw. Following contact of the sperm and said composition for the defined period of time and within the defined temperature, the sperm sample plus the composition are return to either the original or an unused insemination straw and inseminated directly into a receptive female.

A second embodiment of a kit requires that the composition be prepare in multiple dosages. That is, the composition is provided in concentrated form, either in solution or lyophilized, and packaged such that when a multiple sperm sample is added to the composition container, or the composition is added to the sperm sample, the resulting composition/semen solution is of the appropriate physiological concentration. Following contact of the sperm and said composition for the defined period of time and within the defined temperature, the sperm sample plus the composition are individually aliquot and packaged at the appropriate required sperm dosage. This embodiment could be used to prepare frozen gender-biased semen utilizing standard cryopreservation methodology. A second embodiment would be to chill the gender-biased semen to 5-18 degrees Celsius short-term storage, transport, or immediate use.

Methods of Use

In practicing the subject method, a sample of living sperm and the composition of matter are combined and incubated to form a reaction mixture during which the sperm are in contact with the composition. The reaction mixture is incubated under the appropriate conditions to maintain cell viability and/or sperm fertility. The temperature is generally at or near body temperature, e.g. 35-38° C. for cattle, and the time is generally less than 60 minutes but is experimentally determined, and varies with the species, sperm concentration, volume of the sperm sample, and with other factors such as type of diluent, and whether the sperm have been frozen, chilled, or freshly collected. The concentration of the composition is experimentally adjusted to the volume and titer of cell or sperm type. For example, commercially available bull semen is diluted with an extender, a buffered saline solution plus a cryoprotectant, gradually cooled, and frozen in liquid nitrogen and stored in single insemination doses of 2 to $50 \times 10^6$ living sperm in volumes of 0.25 mL or 0.50 mL. Dosage of the composition is adjusted to the volume of the semen sample and sperm concentration, such that the embodiment is maintained at a constant physiological concentration within the sperm storage medium.

Other embodiments of this invention are for breeding "induced ovulators". These include the rabbits, felines, ferrets, bears and camelid species. In these species, ovulation is induced by copulation and the seminal fluid of the male. As such the meth of artificial breeding are modified from the tradition AI methods employed in "spontaneous ovulators" (cattle, sheep, horses, and pigs). The modified methods for induced ovulators include hand-mating (natural insemination), copulation with vasectomized males, and introduction of seminal fluid prior to insemination of a sperm sample. In some embodiments of this invention, the composition is premixed with seminal fluid and inseminated into the reproductive tract of the female. In another embodiment, only the composition is inseminated. This is followed by introduction of sperm by artificial insemination or in some instances, by natural insemination Artisans familiar with the trade of artificial insemination, semen collection and processing, cell culture, and biochemistry would be able to mix, produce and reproduce these compositions following appropriate laboratory methodology, combination of compounds and of preparing cell medium.

Example

The following example is included solely to provide a more complete disclosure of the invention described and claimed herein. The example does not limit the scope of the invention in any fashion.

Chemical and reagents were obtained commercially from Sigma-Aldrich Chemical (St. Louis, Mo., USA).

The preparation of the said composition includes brilliant cresol blue (FIG. 1) that requires the rehydration of physiological quantities: 100 mcM BCB and D-Glucose-6-phosphate ($Na^{++}$salt) at physiological quantities (1-100 mM) rehydrated in modified Tyrodes albumin-lactate-pyruvate medium (TALP) buffered solution pH 7.4.

The components of the composition are mixed to form a rehydrated reaction mixture with a sample of sperm usually in the form of a commercially available frozen-thawed semen sample. As an example, cattle semen is processed and stored (usually frozen) in single insemination doses at a volume of 0.25 mL, 0.50 mL or 1.0 mL and prepared in a commercially available semen extender, i.e. a buffered saline solution containing essential salts, energy substrates, a protein source, a cryoprotectant, and antibiotics. The components of commercially available semen extenders are well documented in the scientific literature.

The mixture of extended semen and the composition of this invention were incubated for 20 minutes at 35-37° C. Following incubation, the exposed semen was washed according to standard methods for in vitro fertilization. The standard 2-step Percoll gradient (90% and 55%) was modified for sperm washing by the addition of 100 mm G-6-P and 1 U/mL of diaphorase. Following centrifugation, the motile sperm fraction was used for in vitro insemination of bovine oocytes. Fertilized oocytes were cultured according to standard methods for bovine embryos for 5-7 days. These were sexed at day 5-7 using a standard PCR embryo sexing protocol. Control sperm underwent the same washing process without exposure to the composition of this invention. Data was pooled over 18 repetitions/N=250 and the average % of male embryo were as follows: Control, 52% male embryos; Treated, 72% male embryos.

REFERENCES

Hoppe, P. C. Glucose requirement for mouse sperm capacitation in in vitro. Biol Reprod., 15:39-45 (1976).

Niwa, K. Iritani, A. Effect of various hexoses on sperm capacitation and penetration of rat eggs in vitro. J. Reprod. Fertil. 53: 267-271 (1978).

Mahadevan, M., Miller M., Moutos, D. Absence of glucose decreases human fertilization and sperm movement characteristics in vitro. Hum Reprod 12.119-123 (1997).

Aitken, R., Fisher, H., Fultin. N., Gomez, E., Knox., W., Lewis, B., and Irvine, S. Reactive oxygen species generation by human spermatozoa is induced by exogenous NADPH and inhibited by the flavoprotein inhibitors dipheneylene idonium and quinacrine. Mol Reprod Dev 47:468-482 (1997).

Urner F. and Sakkas D. A possible role for the pentose phosphate pathway of spermatozoa in gamete fusion in the mouse. Biol Reprod 60, 733-739 (1999).

Setchell, B., Scott, T, Voglmayr, J., and Waites, G. Characteristics of testicular spermatozoa and the fluid which transports them into the epididymis. Biol Reprod 1:40-66 (1969).

Tiffin, G., Rieger, D., Betteridge, K., Yadav, B., King W. Glucose and glutamine metabolism in pre-attachment cattle embryos in relation to sex and stage of development. J. Reprod Fertil 93:125-132 (1991).

Williams, T. A technique for sexing mouse embryos by a visual colorimetric assay for the X-linked enzyme, glucose-6-phosphate dehydrogenase. Theriogenology 25: 733-739 (1986).

Kimura, K., Spate, L., Green, M., and Roberts, R. Effects of D-glucose concentration, D-fructose, and inhibitors of enzymes of the pentose phosphate pathway on the development and sex ratio of bovine blastocysts. Mol. Reprod and Dev 72: 201-207 (2005),

What I claim as my invention is:

1. A method to produce male offspring in mammals, the method comprising contacting sperm with a composition of matter consisting of a phenoxazine or phenothiazine compound and ionic derivates of such; and a hexose sugar or the phosphorylated hexose ester of such, wherein the amounts of said composition and the duration of contact are effective in modifying, the function of the Y-chromosome bearing sperm and the function of the X-chromosome bearing sperm, wherein said sperm are inseminated into a receptive female.

2. The method of claim 1, wherein said phenoxazine or phenothiazine compound, is selected from those having the structure (FIG. 1) and ionic derivatives thereof, wherein R1 is H, a lower alkyl group or N(R3)2, R2 is N, S, or O, and R3 is H or a lower alkyl group.

3. The method of claim 1, wherein said phenoxazine or phenothiazine compound is Brilliant Cresyl Blue, Brilliant Blue C, or Methylene Blue.

4. The method of claim 1, wherein said hexose sugar is selected from the following: fructose, mannose, glucose, and galactose, and their phosphorylated hexose esters: fructose-6-phosphate, mannose-6-phosphate, D-glucose-6-phosphate, and galactose-6-phosphate.

5. The method of claim 1, wherein a receptive female is inseminated to produce an embryo.

6. The method of claim 1, wherein an in vitro fertilization system is inseminated to produce an embryo.

7. The method of claim 1, wherein the modified sperm are cryopreserved.

8. The method of claim 1, wherein the modified sperm are gender-sorted by flow-cell cytometry following contact with, or in the presence of said composition.

9. The method of claim 1, wherein the modified sperm are preserved by cooling, usually to about 2 to 18 degrees Celsius, and held in a sperm storage medium.

10. A method of claim 1, wherein the composition is introduced into a receptive female prior to artificial or natural insemination.

11. A method of claim 10, wherein the composition includes seminal fluid.

12. A kit for producing male offspring in mammals, the kit comprising in combination, a composition of matter consisting of a phenoxazine or phenothiazine compound and ionic derivatives of such, and a hexose sugar or the phosphorylated hexose ester of such, wherein the composition is held in a suitable container, wherein the amounts contained and the duration of contact are effective in modifying sperm function, wherein the volume of the container is approximately equivalent to the commercial standard volume of sperm, wherein the container has a re-sealable septum, wherein the sperm sample is introduced from the sperm sample container directly into the composition container for the purpose of contacting the composition of matter, wherein the sperm sample is transferred from the composition container back into the original sperm sample container or into a new sperm sample container, wherein the sperm and composition are inseminated into a receptive female; and instructions for use of the kit.

* * * * *